United States Patent
Li

(10) Patent No.: US 9,492,493 B2
(45) Date of Patent: Nov. 15, 2016

(54) SOFTGEL OF NLKJ FOR TREATING PROSTATE DISEASES

(71) Applicant: Dapeng Li, Beijing (CN)

(72) Inventor: Dapeng Li, Beijing (CN)

( * ) Notice: Subject to any disclaimer, the term of this patent is extended or adjusted under 35 U.S.C. 154(b) by 150 days.

(21) Appl. No.: 13/624,137

(22) Filed: Sep. 21, 2012

(65) Prior Publication Data

US 2014/0088011 A1 Mar. 27, 2014
US 2016/0263179 A9 Sep. 15, 2016

Related U.S. Application Data

(63) Continuation of application No. 11/099,780, filed on Mar. 28, 2005, now Pat. No. 8,299,121, which is a continuation of application No. PCT/CN03/00803, filed on Sep. 22, 2003.

(51) Int. Cl.

| | | |
|---|---|---|
| *A61K 31/231* | (2006.01) | |
| *A61K 38/09* | (2006.01) | |
| *A61P 35/00* | (2006.01) | |
| *A61P 13/08* | (2006.01) | |
| *A61K 36/8994* | (2006.01) | |
| *A61K 31/355* | (2006.01) | |
| *A61K 9/48* | (2006.01) | |

(52) U.S. Cl.
CPC ......... *A61K 36/8994* (2013.01); *A61K 9/4825* (2013.01); *A61K 9/4858* (2013.01); *A61K 31/355* (2013.01); *A61K 38/09* (2013.01)

(58) Field of Classification Search
None
See application file for complete search history.

(56) References Cited

U.S. PATENT DOCUMENTS

| | | | | |
|---|---|---|---|---|
| 5,326,757 | A * | 7/1994 | Demopoulos | 514/167 |
| 5,444,089 | A * | 8/1995 | Li | 514/547 |
| 2005/0222249 | A1* | 10/2005 | Li | 514/458 |

OTHER PUBLICATIONS

Gunawardena et al. The Prostate. 44;287-295:2000.*
Yu et al. J Surg Res. 105;65-68:2002.*
Sharifi et al. Clin Thera. 18(4);647-657:1996.*
Conversion Chart. Newagelandmark.com. Downloaded Jul. 26, 2013.*

* cited by examiner

*Primary Examiner* — Amber D Steele
*Assistant Examiner* — Schuyler Milton

(57) ABSTRACT

A softgel of NLKJ for the treatment of prostate diseases, comprising 0.05-1.0 g of NLKJ and 0.05-1.5 mg of an antioxidant, said NLKJ having the following physicochemical parameter: acid value<0.56, iodine value 95.0-107.00, saponification value 185.00-195.00, specific gravity 0.914-0.918 (20° C.), and refractive index 1.470-1.475 (20° C.). The inhibition of the softgel of NLKJ on the growth of prostate cancer in combination with the injection of Lupron is stronger than that of each of them used alone.

6 Claims, No Drawings

SOFTGEL OF NLKJ FOR TREATING PROSTATE DISEASES

CROSS REFERENCE OF RELATED APPLICATION

This is a Continuation application of an application having an application Ser. No. 11/099,780 filed on Mar. 28, 2005, which is in a U.S. National Stage under 35 U.S.C 371 of the International Application PCT/CN2003/000803, filed on Sep. 22, 2003, which claims priority under 35 U.S.C. 119(a-d) to CN 02137311.6, filed on Sep. 28, 2002.

BACKGROUND OF THE INVENTION

1. Field of Invention

The invention refers to a softgel. More specially, the invention refers to a softgel of neutral lipids obtained from kernels of Job's tears for the treatment of prostate diseases.

2. Description of Related Arts

Neutral lipids obtained from kernels of Job's tears (*Coix lacryma-jobi*) (abbreviated to NLKJ hereinafter) having anti-tumor activities and enhancing immunological functions were disclosed in Chinese Patent 93117605.0. An emulsion of NLKJ mainly used via intravenous or intraartery injection was disclosed in Chinese Patent 93100735.6. Neutral lipids from kernels of Job's tears and the anti-tumor pharmaceutical composition containing same were disclosed in U.S. Pat. No. 5,444,089. Neutral lipids from kernels of Job's tears, a process for the preparation thereof and the pharmaceutical composition containing same were disclosed in European Patent 0 588 621. However, in previous documents, neither softgel of NLKJ nor the application thereof in treating prostate diseases was described.

Thus, one object of the invention is to provide a softgel of NLKJ for the treatment of prostate diseases.

The second object of the invention is to provide a kit for the treatment of prostate diseases.

The third object of the invention is to provide a method for the treatment of prostate diseases.

SUMMARY OF THE INVENTION

The invention provides a softgel of NLKJ for the treatment of prostate diseases, comprising from 0.05 to 1.0 g of NLKJ and from 0.05 to 1.5 mg of an antioxidant, said NLKJ having the following physicochemical parameter: acid value<0.56, iodine value 95.0-107.00, saponification value 185.00-195.00, specific gravity 0.914-0.918 (20° C.), and refractive index 1.470-1.475 (20° C.).

The NLKJ in the softgel of the invention is neutral lipids obtained from kernels of Job's tears by using the method described in Chinese Patent 93117605.0. The standards of the softgel can be those for oral or injection administration.

Preferably, the antioxidant in the softgel is Vitamin E.

Preferably, the softgel of the invention contains NLKJ 0.45 g and Vitamin E 0.3375 mg.

The invention also provides a kit for the treatment of prostate diseases, comprising softgels of NLKJ and Instructions for use.

The invention further provides a method for the treatment of prostate diseases in a mammal, comprising administering to said mammal a therapeutically effective amount of the softgel of NLKJ of the invention.

It was written in the Instructions that the daily oral dosage of the softgel of NLKJ is 0.1-1.0 g/kg; preferably, it is divided into 3-4 times; more preferably, it is administered in combination with the injection of Lupron, 3.75 mg, once per 4 weeks, to enhance the effects.

The use of the NLKJ softgels of the invention in the treatment of prostate diseases, including cancer, has shown merits in an easy administration and a higher curative effect, especially, significant inhibition on the growth of prostate cancer in combination with the injection of leuprolide acetate (Lupron®). The inhibition of this combination on the tumor is stronger than that of each of them used alone.

These and other objectives, features, and advantages of the present invention will become apparent from the following detailed description, the accompanying drawings, and the appended claims.

DETAILED DESCRIPTION OF THE PREFERRED EMBODIMENT

The technical solution of the invention is exemplified in the following examples.

EXAMPLE OF PREPARATION

Dosage: NLKJ 4500 g and Vitamin E 3.375 g (antioxidant) were weighed respectively. Vitamin E was added into NLKJ at room temperature and stirred to become a clear and transparent solution.

Making a sol: The shell-forming materials were weighed in the proportion of gelatin: water: glycerin: ethyl p-hydroxybenzenecarboxylate (preservative)=1:1:0.4:0.001, and stirred at 80° C. to form a sol, which was deaerated under a decreased pressure and maintained at 60° C.

Softgels were formed in a pill compressing machine. Then, they were rubbed so as to remove the oil thereon, and then dried and regulated, to obtain 10000 softgels.

EXPERIMENT EXAMPLES

Experiment Example 1

Inhibition of NLKJ Softgels on the Growth of Human Prostate Cancer in an Animal Model Experiment Drug:

NLKJ softgels (NLKJ for injection), Batch No. 20010412;

Kanglaite Injection (Product of Zhejiang Kanglaite Pharmaceutical Co. LTD, containing NLKJ 10 g/100 ml), Batch No. 0011281-1.

Experiment Animal:

30 male BALB/C nude mice (SPF grade), weighted 17-18 g, provided by Shanghai Cancer Institute (Certification of Quality No. 02-30-1 Sh. Med. Anim.).

Grafting Tumor: Human prostate cancer (PC-3M), sub-cultured by Pharmacological Department, Shanghai Institute of Pharmaceutical Industry.

Experiment Method:

Well grown PC-3M tumors were homogenized in normal saline (1:4). The nude mice were inoculated subcutaneously in the axilla with 0.2 ml/mouse of the homogenate, then grouped randomly as follows:

1) Control Group (Normal saline);
2) NLKJ softgel (5 ml/kg, p.o.×10 d);
3) NLKJ softgel (10 ml/kg, p.o.×10 d);
4) Kanglaite Injection (25 ml/kg, i.v.×10 d);
5) Cyclophamide (CTX) (100 mg/kg, ip.×3 (d1, d5, d9)).

The treatment started from the second day after inoculation. On the 21$^{th}$ day after inoculation, the animals were sacrificed via dislocation of cervical vertabra and dissected to pick off the tumors. The weights of tumors were compared among the groups. The result was judged based on the formula:

$$IR\% = \frac{\overline{X}_{con} - \overline{X}_{treat}}{\overline{X}_{con}} \times 100\%$$

IR: Inhibition Rate of Tumor; $\overline{X}_{con}$: Average weight of tumors of the control group; $\overline{X}_{treat}$: Average weight of tumors of the treatment group.

Experiment Result: The results are shown in Table 1.

Lupron (Takeda Chemical Industries, Ltd., Osaka, Japan 541), Batch No. 47978 AP.

Experiment Animal:

Male BALB/C nude mice (SPF grade), weighted 19-21 g, provided by Shanghai Cancer Institute (Certification of Quality No. 02-30-1 Sh. Med. Anim.).

Grafting Tumor: Human prostate cancer (PC-3M), sub-cultured by Pharmacological Department, Shanghai Institute of Pharmaceutical Industry.

Experiment Method:

Well grown PC-3M tumors were homogenized in normal saline (1:4). The nude mice were inoculated subcutaneously in the axilla with 0.2 ml/mouse of the homogenate, then grouped randomly as follows:

1) Control Group (Normal saline);
2) NLKJ softgel (5 ml/kg, p.o.×10 d);
3) NLKJ softgel (10 ml/kg, p.o.×10 d);
4) Lupron (0.75 mg/kg, s.c.×1);
5) Lupron (1.50 mg/kg, s.c.×1);

TABLE 1

Inhibition of NLKJ softgel on human prostate cancer (PC-3M)

| Group | Dosage (ml/kg) | Treatment method | n Beg | n End | Body weight (g) Beg | Body weight (g) End | Tumor Weight (g) ($\overline{x}$ ± SD) | Inhibition Rate (%) |
|---|---|---|---|---|---|---|---|---|
| Control (Normal saline) | 25 | po × 10 | 6 | 6 | 17.5 | 18.3 | 1.55 ± 0.15 | |
| CTX | 100 mg/kg | ip × 3 (d 1, 5, 9) | 6 | 6 | 17.0 | 17.8 | 0.12 ± 0.04** | 92.47 |
| Kanglaite Injection | 25 | iv × 10 | 6 | 6 | 17.2 | 18.3 | 0.75 ± 0.10** | 51.61 |
| NLKJ softgel | 5 | po × 10 | 6 | 6 | 17.3 | 17.2 | 1.00 ± 0.14** | 35.48 |
| NLKJ softgel | 10 | po × 10 | 6 | 6 | 18.0 | 18.8 | 0.63 ± 0.10** | 59.14 |

Compared with Control;

**$p < 0.01$.

It is shown in the above Table 1 that, in the animal model, the NLKJ softgel of the invention (10 ml/kg) has an obvious effect of inhibition on the growth of human prostate cancer. The inhibition rate reached 59.14%, which is higher than that of Kanglaite Injection, 25 ml/kg, i.v. (51.61%).

Experiment Example 2

Inhibition of NLKJ Softgels in Combination with Lupron on the Growth of Human Prostate Cancer in Animal Models Experiment Drug:

NLKJ softgels (NLKJ for injection), Batch No. 011209;

6) NLKJ softgel (5 ml/kg, p.o.×10 d)+Lupron (0.75 mg/kg, s.c.×1);
7) NLKJ softgel (10 ml/kg, p.o.×10 d)+Lupron (1.50 mg/kg, s.c.×1).

The NLKJ softgels (NLKJ for injection) were administrated from the second day after the inoculation of mice through a stomach-tube, once a day, for 10 days. Lupron was given subcutaneously on the second day of the inoculation. On the 21$^{th}$ day after inoculation, the animals were sacrificed via dislocation of cervical vertabra and dissected to pick off the tumors. The weights of tumors were compared among the groups. The results were shown in Table 2.

TABLE 2

Inhibition of NLKJ softgel on human prostate cancer (PC-3M)

| Group | Dosage (ml/kg) | Treatment method | n Beg | n End | Body weight (g) Beg | Body weight (g) End | Tumor Weight(g) (x̄ ± SD) | Inhibition Rate(%) |
|---|---|---|---|---|---|---|---|---|
| Control (Normal saline) | 25 | po × 10 | 6 | 6 | 19.6 | 22.0 | 1.48 ± 0.17 | |
| NLKJ softgel | 5 | po × 10 | 6 | 6 | 19.0 | 21.5 | 1.18 ± 0.34 | 20.22 |
| | 10 | po × 10 | 6 | 6 | 20.0 | 21.8 | 0.82 ± 0.12** | 44.94 |
| Lupron | 0.75 | sc × 1 | 6 | 6 | 19.8 | 19.8 | 0.93 ± 0.23** | 37.08 |
| | 1.50 | sc × 1 | 6 | 6 | 19.5 | 20.3 | 0.77 ± 0.14** | 48.31 |
| NLKJ softgel + Lupron | 5 0.75 | po × 10 sc × 1 | 6 6 | 6 6 | 19.7 | 21.3 | 0.63 ± 0.16** | 57.30 |
| NLKJ softgel + Lupron | 10 1.50 | po × 10 sc × 1 | 6 6 | 6 6 | 19.4 | 21.2 | 0.55 ± 0.44** | 62.92 |

Compared with Control:
**p < 0.01.

It is shown in the above table that the inhibition rates of the NLKJ softgel of the invention, 5 ml/kg and 10 ml/kg, p.o., q.d., for ten days, are 20.22% and 44.94%, respectively; those of Lupron, 0.75 mg/kg and 1.50 mg/kg, s.c., are 37.08% and 48.31%, respectively; whereas that of the combination of NLKJ softgel of the invention (10 ml/kg, po×10) with Lupron (1.50 mg/kg, sc×1) is 62.92%. From the result of the experiment, it is suggested that there is an enhancement on the inhibition of human prostate cancer in the combination of NLKJ softgel with Lupron.

It has also been found in the research that the NLKJ softgel of the invention has some therapeutic effects on other prostate diseases such as prostatomegaly.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method for the treatment of prostate diseases excluding prostatomegaly and prostate cancer in a mammal, comprising administering to said mammal a therapeutically effective amount of a softgel of neutral lipids obtained from kernels of Job's tears (Coix lacryma-jobi) (NLKJ) comprising from 0.05 g to 1.0 g of NLKJ and from 0.05 mg to 1.5 mg of an antioxidant, said NLKJ having the following physicochemical parameter: acid value <0.56, iodine value 95.0-107.00, saponification value 185.00-195.00, specific gravity 0.914-0.918 (20° C.), and refractive index 1.470-1.475 (20° C.).

2. The method according to claim 1, wherein said therapeutically effective amount of the softgel of NLKJ is 0.1-1.0 g/kg/day.

3. The method according to claim 1, wherein said therapeutically effective amount of the softgel of NLKJ is divided into 3-4 times.

4. The method according to claim 1, wherein said therapeutically effective amount of the softgel of NLKJ is in combination with the injection of leuprolide, 3.75 mg, once per 4 weeks.

5. The method according to claim 1, wherein said antioxidant is Vitamin E.

6. The method according to claim 1, comprising NLKJ 0.45 g and Vitamin E 0.3375 mg.

* * * * *